US00PP27062P2

(12) United States Plant Patent
Pluta et al.

(10) Patent No.: US PP27,062 P2
(45) Date of Patent: Aug. 16, 2016

(54) BLACK CURRANT PLANT NAMED 'TIHOPE'

(50) Latin Name: *Ribes nigrum*
Varietal Denomination: Tihope

(71) Applicants: Stanislaw Pluta, Skierniewice (PL); Edward Zurawicz, Skierniewice (PL)

(72) Inventors: Stanislaw Pluta, Skierniewice (PL); Edward Zurawicz, Skierniewice (PL)

(73) Assignee: Instytut Ogrodnictwa, Skierniewice (PL)

( * ) Notice: Subject to any disclaimer, the term of this patent is extended or adjusted under 35 U.S.C. 154(b) by 184 days.

(21) Appl. No.: 13/998,944

(22) Filed: Dec. 23, 2013

Related U.S. Application Data

(60) Provisional application No. 61/848,169, filed on Dec. 26, 2012.

(51) Int. Cl.
*A01H 5/08* (2006.01)

(52) U.S. Cl.
USPC ..... Plt./156

(58) Field of Classification Search
USPC ..... Plt./156
See application file for complete search history.

(56) References Cited

PUBLICATIONS

Pluta et al. Journal of Berry Research 2: 23-31, 2012.*

* cited by examiner

*Primary Examiner* — Keith Robinson
(74) *Attorney, Agent, or Firm* — Penny J. Aguirre

(57) ABSTRACT

A new cultivar of *Ribes nigrum*, 'Tihope', that is characterized by its upright plant habit and vigorous plant growth, its high fruit productivity, its large sized fruit, its high quality fruit that is high in anthocyanin concentration and medium in ascorbic acid content and acidity, its high resistance in the field to white pine blister rust (*Cronartium ribicola*) and powdery mildew (*Sphareotheca mors-uvae*), and its high level of winter hardiness.

2 Drawing Sheets

Botanical classification: *Ribes nigrum.*
Cultivar designation: 'Tihope'.

BACKGROUND OF THE INVENTION

The present invention relates to a new and distinct cultivar of *Ribes nigrum* named 'Tihope' and is hereinafter referred to by the cultivar name 'Tihope'. 'Tihope' represents a new cultivar of black currant grown for fruit production.

The new cultivar derived from a controlled breeding program by the Inventors in Skierniewice, Poland. The Inventors made a cross in 1991 between 'Titania' (U.S. Plant Pat. No. 11,439) as the female parent and reference no. P9/11/14, as the male parent. The Inventors selected 'Tihope', breeding reference no. PC-425, in 1996 as a single unique plant amongst the seedlings that resulted from the above cross.

Asexual propagation of the new cultivar was first accomplished by one of the Inventors by hardwood cuttings in Skierniewice, Poland in 2012. Asexual propagation by hardwood cuttings of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Tihope' as a new and unique cultivar of *Ribes nigrum.*

1. 'Tihope' exhibits an upright plant habit and vigorous plant growth.
2. 'Tihope' exhibits high fruit productivity.

3. 'Tihope' exhibits large sized fruit.
4. 'Tihope' exhibits high quality fruit that is high in anthocyanin concentration and medium in ascorbic acid content and acidity.
5. 'Tihope' exhibits high resistance in the field to white pine blister rust (*Cronartium ribicola*) and powdery mildew (*Sphareotheca mors-uvae*).
6. 'Tihope' exhibits a high level of winter hardiness.

'Tihope' can be readily compared to its parent plants. 'Titania', the female parent, differs from 'Tihope' in having slightly more vigorous plant growth, in having a less spreading plant habit, in having lower fruit quality and productivity, and in being more susceptible to fungal diseases. P9/11/14, the male parent, differs from 'Tihope' in having less vigorous plant growth, in having a less upright plant habit, in having lower fruit quality and productivity, and in being more susceptible to fungal diseases. 'Tihope' can be most closely compared to the *Ribes* cultivars 'Ben Hope' (not patented) and 'Ben Lomond' (not patented). 'Ben Hope' is similar to 'Tihope' in having a vigorous growth rate, in having high quality fruit, and in being very winter hardy. 'Ben Hope' differs from 'Tihope' in having leaves that are less green in color, in having a less spreading plant habit, in having fruit that is smaller in size, and in being more susceptible to fungal diseases. 'Ben Lomond' is similar to 'Tihope' in having high quality fruit that is large in size, in having high fruit productivity, and in its ripening time. 'Ben Lomond' differs from 'Tihope' in having leaves that are darker green in color, in having a less upright plant habit, in being more susceptible to fungal diseases, and in being much less winter hardy.

BRIEF DESCRIPTION OF THE DRAWINGS

The accompanying colored photographs illustrate the overall appearance and distinct characteristics of the new *Ribes* cultivar. The photographs were taken of three year-old plants of the new cultivar as grown outdoors in a field in Skierniewice, Poland.

Figure 1:
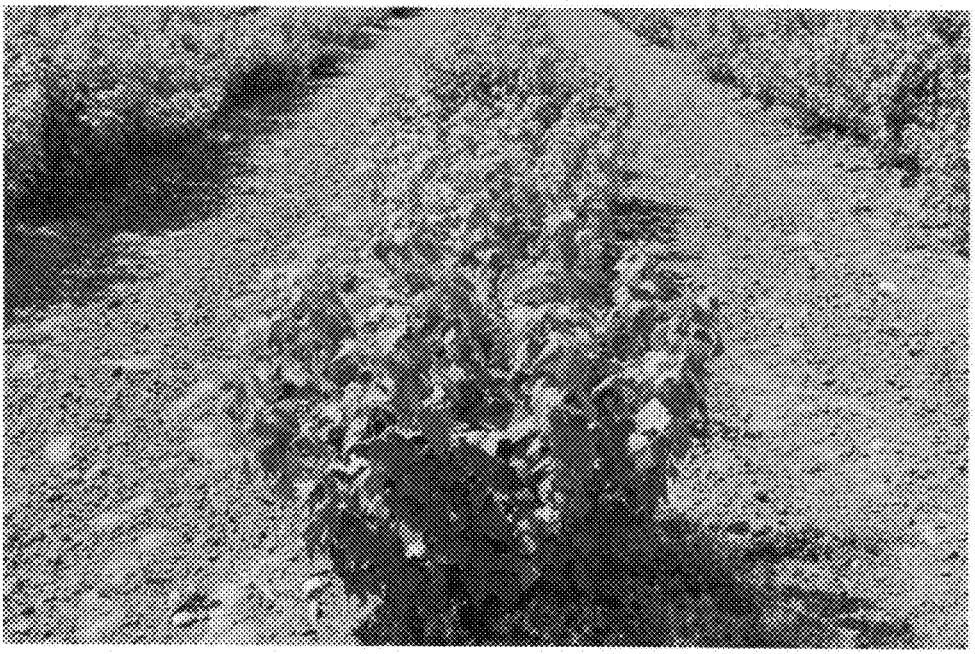

The photograph in FIG. 1 provides a view of the plant habit of 'Tihope'.

Figure 2:
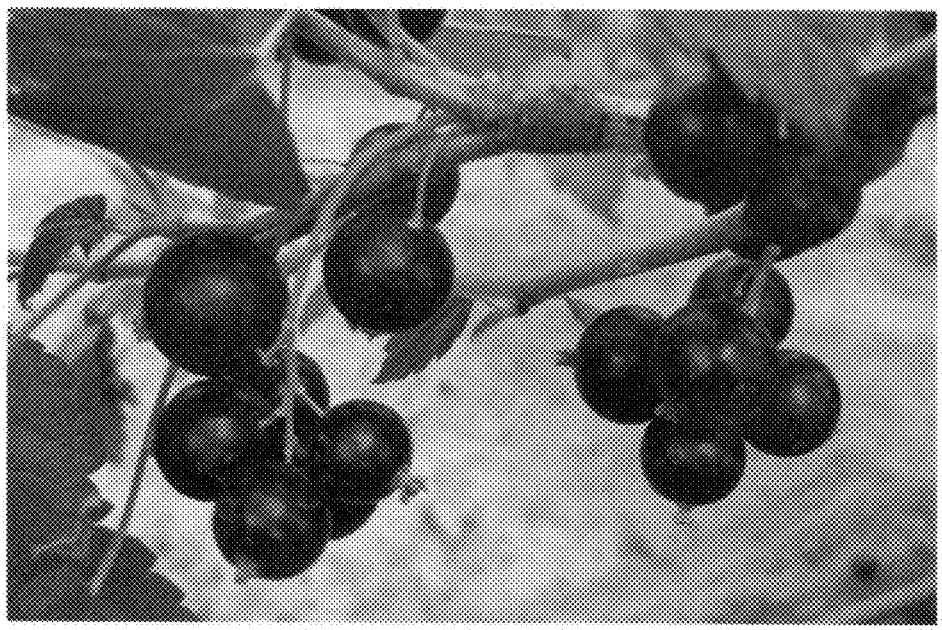

The photograph in FIG. 2 provides a close-up view of a fruiting branch of 'Tihope'.

Figure 3:
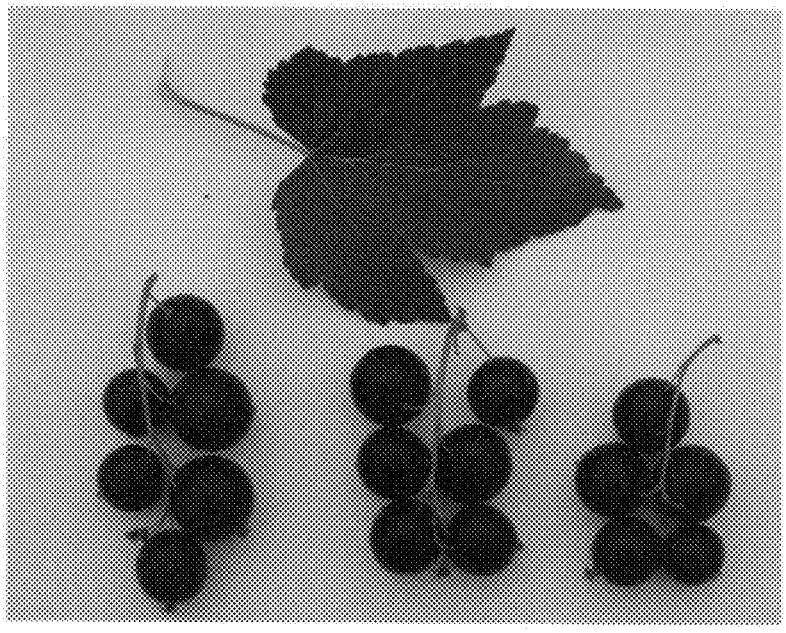

The photograph in FIG. 3 provides a close-up view of mature fruit and a mature leaf of 'Tihope'.

The colors in the photographs are as close as possible with digital photography techniques available, the color values cited in the detailed botanical description accurately describe the colors of the new cultivar of *Ribes*.

DETAILED BOTANICAL DESCRIPTION OF THE PLANT

The following is a detailed description of plants three years in age as grown outdoors in a trial field in Skierniewice, Poland. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Late April to early May in Skierniewice, Poland.

*Plant type*.—Perennial, fruit producing shrub.

*Plant habit*.—Tall and slightly spreading.

*Height and spread*.—Reaches about an average of 1.25 m in height and 1.84 m in width.

*Cold hardiness*.—At least in U.S.D.A. Zone 6.

*Diseases and pests*.—High resistance in the field to white pine blister rust (*Cronartium ribicola*) and powdery mildew (*Sphareotheca mors-uvae*) has been observed.

*Roots*.—Fibrous and 162D in color.

*Root development*.—About 10 days to initiate roots and 2 months to produce a young rooted plant.

*Propagation*.—Hardwood cuttings.

*Growth rate*.—Vigorous.

Stem description:

*Stem*.—Strong, 177B and 196B and 198C in color; new growth, 144A in color, surface is smooth on new growth and smooth bark-like when mature, branches up to 1.20 m in length and an average of 1.65 m in width.

*Stem number*.—An average of 20 basal shoots per 3 year-old plant.

*Leaf bud shape*.—Obclavate, bracts imbricate.

*Leaf bud size*.—Average of 7.1 mm in length, 4.8 mm in width.

*Leaf bud position relative to shoot*.—Slightly held out.

*Leaf bud burst*.—Begins in late March to early April in Poland.

*Leaf bud apex*.—Rounded.

*Number of leaf buds*.—On a 50 cm long stem average of 12.3 buds, ranging from 11 to 13 buds, per stem.

*Bracts*.—Deltoid in shape, apex retuse to subacute, base truncate, average 1.8 cm in width, 3.3 cm in length, margin entire and fimbriate, young inner surface 145A, flushed with 181A in color, young outer surface 145A in color, older bracts inner and outer surface 181A in color.

Foliage description:

*Leaf shape*.—Ovate, five lobed with extended center lobe.

*Leaf division*.—Simple, leaf not divided.

*Leaf base*.—Cordate to auriculate, weakly opened.

*Leaf apex*.—Subacute.

*Leaf venation*.—Pinnate, color on upper and lower surface 142A, slightly puberulent with fine minute hairs on lower surface.

*Leaf margins*.—Acute, lobed with lobe margins serrate.

*Leaf attachment*.—Petiolate.

*Leaf arrangement*.—Alternate clusters of leaves.

*Leaf orientation*.—Slightly downward.

*Leaf surface*.—Upper surface glabrous, lower surface slightly puberulent with fine minute hairs and glandular.

*Leaf color*.—Young upper surface; a blend of N144A and 143A, young lower surface; N144A, mature upper and lower surface; 143A to 143B.

*Leaf size*.—Medium to large, an average of 13 cm in length, an average of 14 cm in width.

*Leaf quantity*.—About 22 per 103 cm of stem length.

*Petioles*.—Round in shape, an average of 4.86 cm in length and 2.5 mm in width, a blend of 143A and 149A, surface smooth.

*Stipules*.—None observed.

Inflorescence description:

*Bloom season*.—Approximately April to May in Skierniewice, Poland.

*Inflorescence*.—Drooping raceme of single and double flowers, average of 2.74 cm in length and 1.22 cm in width, 12 racemes per stem 40 cm in length.

*Lastingness of inflorescence*.—8 to 12 days depending on weather conditions at time of bloom.

*Pedicels*.—Round in shape, 2 mm in width, 2.2 cm in length, a blend of 149B and 181A, strong, surface texture smooth.

*Peduncles*.—Round in shape an average of 5 mm in length and 1 mm in width, strong, surface is smooth, a blend of 143A and 181A and 180A, turning 150A towards the tip.

*Flowers*.—Campanulate, 5 to 8 flowers per raceme.

*Flower buds*.—Ovate in shape, 4 to 6 mm in length, 4 mm in width, color; middle section a blend of 149A and 145C, base is 145A, suffused with 178A.

*Flower size*.—Average of 6 mm in length, 5.8 mm in width.

*Flower number*.—An average of 10 flowers per raceme (inflorescence).

*Sepals*.—5, strongly recurved, 2 mm in width, 3 mm in length fused at base, color on outer and inner surface; a middle section N144C, tips a blend of 63C, 75B and 73A, suffused with 178A at the base in color, rounded apex, margins entire, sparsely pubescent on upper surface and pubescent on lower surface.

*Petals*.—5 fused in hypanthium, 4 mm in length, 3 mm in width, 145B to 145C in color on inner and outer surface, upper surface smooth (texture) and smooth (texture) lower surface.

*Androecium*.—Epipetalous, anthers are ovate in shape 11C in color, 8 mm in length, 6 mm in width, filaments are 3 mm in length, 6 mm in width, 11D in color.

*Gynoecium.*—5 fused in hypanthium, style is 4 mm in length, 0.7 mm in width, 14BA in color, ovary is inferior, 3 mm in length and width, round in shape, 145B in color, bifid stigma is minute and 145B in color.

Fruit description:

*Fruit number.*—65 to 84 fruits per branch 94 cm long.

*Fruit yield.*—1.95 kg per plant in Skierniewice, Poland on 5 year-old plants.

*Fruit set.*—High, 87%.

*Fruit size.*—Medium to large sized fruit, average of 1.54 cm in diameter and 1.52 cm in height.

*Fruit weight.*—Ranges from 0.9 to 1.3 g/berry.

*Fruit chemistry.*—High in acidity, anthocyanins, and ascorbic acid, averages: Brix 16, specific gravity 1.045, tartaric and 36.4 g/L citric, anthoncyanins 286 (517 nm), ascorbic acid 129 ml/100 ml.

*Position of maximum diameter.*—Midway between proximal and distal ends.

*Fruit shape.*—Globose.

*Fruit symmetry.*—Symmetric.

*Persistence of calyx.*—Persistent at harvest, 177A in color, 2 mm in length.

*Surface.*—Glossy, smooth except for slightly protruding lenticels.

*Lenticels.*—22 to 75 per fruit, 198D in color.

*Waxiness of skin.*—Very light.

*Thickness of skin.*—Medium.

*Skin color.*—Immature 145A, maturing 181A, mature 202A.

*Color of flesh.*—N79A.

*Fruit maturity date.*—Mid to late fruit ripening, first harvest date about July 15$^{th}$, range of harvest period one week.

*Seed.*—Oblong in shape, 36 per fruit, 2.5 mm in length, 1.3 mm in width, 200C in color.

*Firmness (without skin).*—Medium.

*Texture of flesh.*—Pulpy, juicy.

*Cropping frequency.*—Regular.

*Flavor.*—Medium acid.

*Fruit use.*—Suitable for fresh fruit and for processing for use in concentrates, frozen foods, and preserves.

*Juice yield.*—18 ml/100 berries.

*Fruit keeping quality.*—Good.

It is claimed:

1. A new and distinct cultivar of *Ribes nigrum* plant named 'Tihope' as herein illustrated and described.

* * * * *